United States Patent [19]
Kohayakawa

[11] Patent Number: 5,825,460
[45] Date of Patent: Oct. 20, 1998

[54] VISUAL FUNCTION MEASURING APPARATUS

[75] Inventor: Yoshimi Kohayakawa, Yokohama, Japan

[73] Assignee: Canon Kabushiki Kaisha, Tokyo, Japan

[21] Appl. No.: 429,158

[22] Filed: Apr. 26, 1995

[30] Foreign Application Priority Data

Apr. 30, 1994 [JP] Japan .................................. 6-113788
Sep. 13, 1994 [JP] Japan .................................. 6-246880

[51] Int. Cl.⁶ ............................................. A61B 3/02
[52] U.S. Cl. .......................... 351/237; 351/222; 351/239
[58] Field of Search ............................. 351/222, 237, 351/238, 239, 242, 200, 203

[56] References Cited

U.S. PATENT DOCUMENTS

| | | | |
|---|---|---|---|
| 3,861,790 | 1/1975 | Tamura | 351/237 |
| 4,511,228 | 4/1985 | von Gierke et al. | 351/237 |
| 4,697,895 | 10/1987 | Sekiguchi et al. | 351/243 |
| 4,820,037 | 4/1989 | Kohayakawa et al. | 351/311 |
| 5,037,194 | 8/1991 | Kohayakawa et al. | 351/224 |
| 5,144,346 | 9/1992 | Nakamura et al. | 351/208 |
| 5,231,430 | 7/1993 | Kohayakawa | 351/243 |
| 5,237,351 | 8/1993 | Kohayakawa et al. | 351/243 |
| 5,325,134 | 6/1994 | Kohayakawa | 351/212 |

*Primary Examiner*—Huy Mai
*Attorney, Agent, or Firm*—Fitzpatrick, Cella, Harper & Scinto

[57] ABSTRACT

A visual function measuring apparatus includes a visual target displaying device for presenting visual targets of different sizes successively to an eye to be examined, and a response inputting lever for inputting the response of an examinee to which the visual targets have been presented. The examinee's visual function is measured on the basis of the response input. The apparatus also includes a controller for controlling the device so that the visual targets presented to the examinee by the visual target displaying device may be changed in succession from a smaller visual target to a larger visual target.

15 Claims, 6 Drawing Sheets

S

S

S

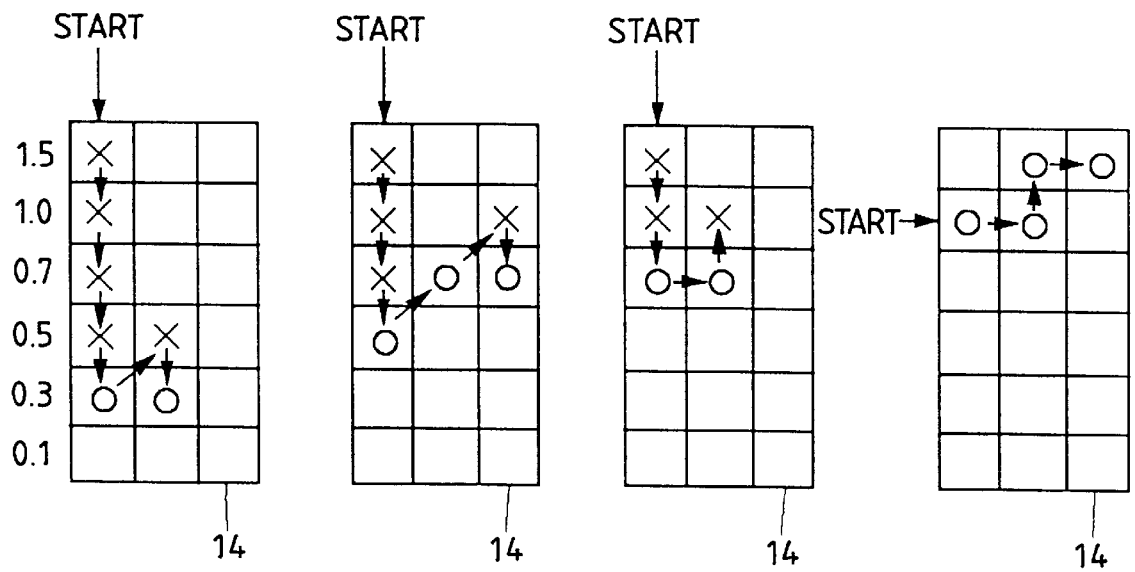
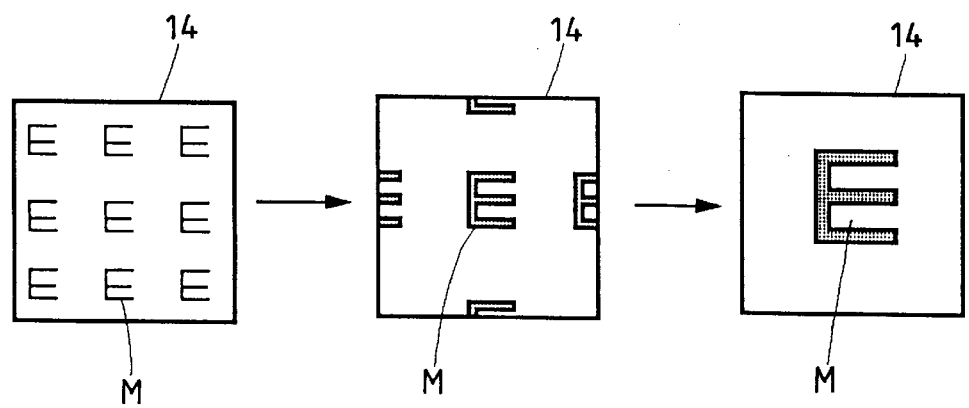

VISUAL FUNCTION MEASURING APPARATUS

BACKGROUND OF THE INVENTION

1. Field of the Invention

This invention relates to a visual function measuring apparatus for use for optometry in ophthalmic hospitals.

2. Related Background Art

In an automatic optometer according to the prior art, visual targets such as Landolt rings are presented one by one and an examinee responds to the direction thereof, and the response is judged by a computer to thereby determine the eyesight of the examinee.

In the case of the automatic optometer according to the prior art, however, the examination is begun with a larger visual target and after the examinee's response, the visual target is sequentially changed to a smaller visual target, and this has led to the problem that the frequency of response becomes great and much time is required for measurement.

SUMMARY OF THE INVENTION

It is an object of the present invention to solve the above-noted problem and to provide an automatic visual function measuring apparatus in which the frequency of responses of an examinee is decreased to thereby shorten the time necessary for measurement.

Other objects of the present invention will become apparent from the following detailed description of some embodiments of the invention.

BRIEF DESCRIPTION OF THE DRAWINGS

FIGS. 8A, 8B, 8C and 8D illustrate the order of presentation of visual targets.

FIGS. 9A, 9B and 9C are illustrations of a visual target in a third embodiment of the present invention.

DESCRIPTION OF THE PREFERRED EMBODIMENTS

Figure 1:
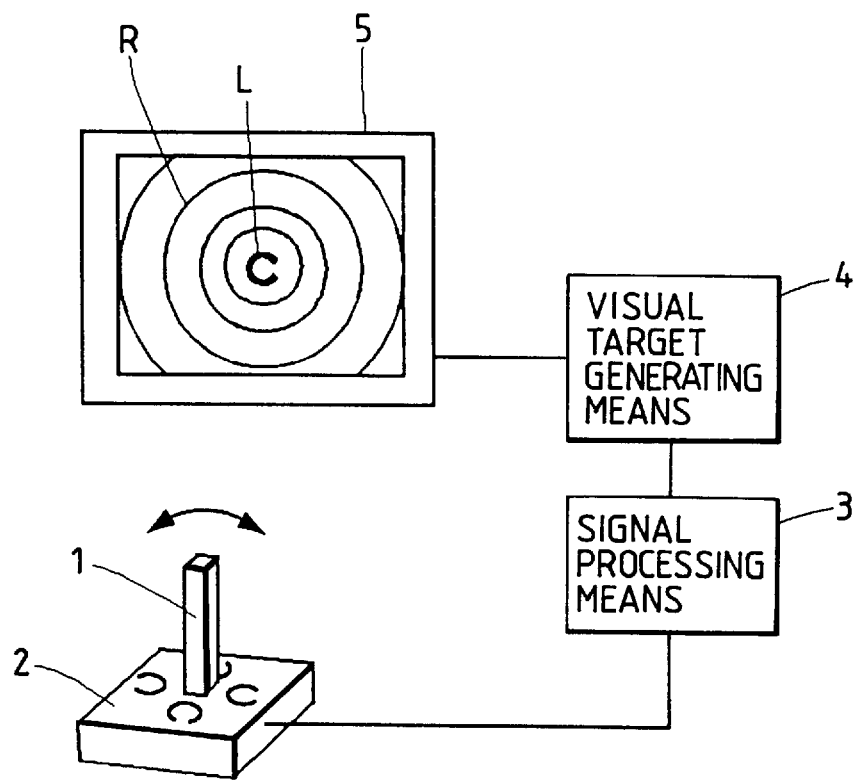
FIG. 1 shows the construction of a first embodiment of the present invention.

The present invention will hereinafter be described in detail with respect to some embodiments thereof shown in the drawings.

Referring to FIG. 1 which shows the construction of a first embodiment, the output of response means 2 having an operating rod 1 is connected to signal processing means 3 including a computer. The output of the signal processing means 3 is connected through visual target generating means 4 to display means 5 comprising a CRT, a liquid crystal plate or the like for displaying a visual target mark L. The signal processing means 3 is designed to control for the presentations the visual target marks responding to signals from the response means 2 by which an examinee inputs a response, and calculates the result of measurement such as an eyesight value.

Figure 2A:
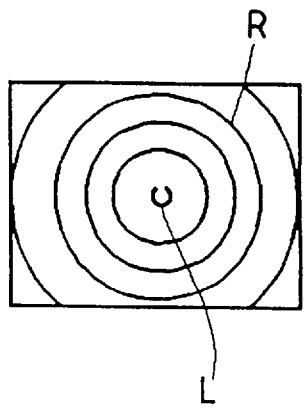
FIGS. 2A, 2B and 2C are illustrations of visual targets for optometry.
Figure 2B:
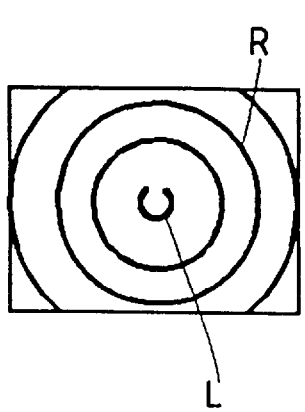
Figure 2C:
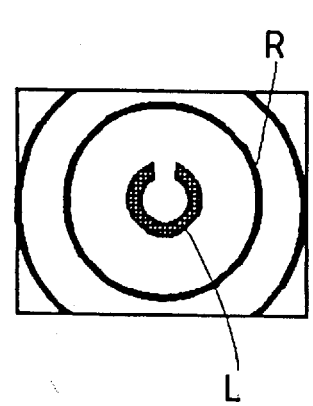
Figure 3:
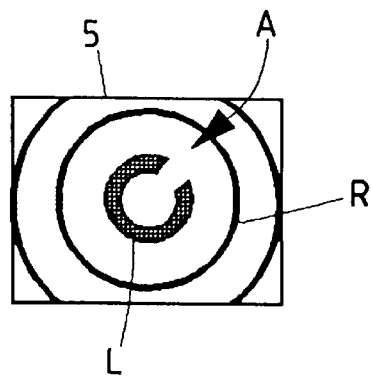
FIG. 3 is an illustration of a response mark in a visual target.

By a signal from the signal processing means 3, the visual target generating means 4, including a bit map memory, generates a visual target pattern for optometry on the display means 5. The visual target pattern displayed on the display means 5 is comprised of a Landolt ring L in the center and multiple rings R surrounding it, and the visual target pattern gradually varies with time from the initial state of FIG. 2A to the states of FIGS. 2B and 2C. That is, its image is enlarged, its pattern becomes larger and its line width becomes thicker. The examinee operates the operating rod 1 of the response means 2 in order to input the direction of the Landolt ring L when he or she visually recognizes that direction. A response mark A is then displayed on the screen of the display means 5 as shown in FIG. 3 so that examinee can visually confirm the direction in which he or she has responded. When the direction of the response is correct, a Landolt ring L of another direction is presented and in the manner as previously described, it is gradually enlarged from its initial state. When the examinee operates the operating rod 1 for the purpose of response, the enlargement is stopped, and the size of the Landolt ring is fixed for a predetermined number of seconds which is the time required to operate the operating rod 1. When the direction of the response is not correct, the enlargement is again started and is continued until a correct response is obtained. The above mentioned process is repeated with visual targets of three to five different directions.

Figure 4A:
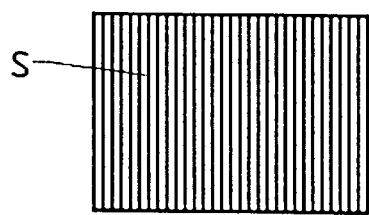
FIGS. 4A, 4B and 4C are illustrations of a stripe pattern visual target with different pitches.
Figure 4B:
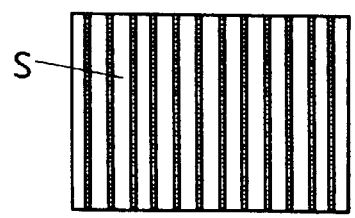
Figure 4C:
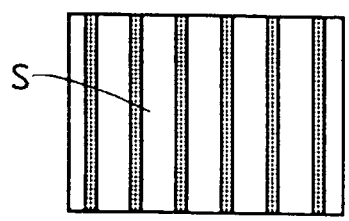
Figure 5:
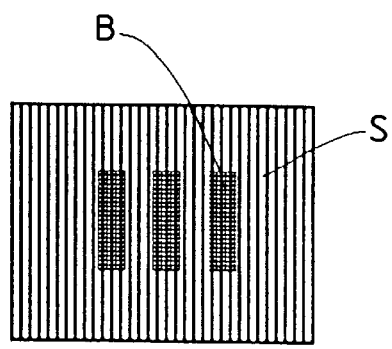
FIG. 5 is an illustration of a response mark in a stripe pattern visual target.

FIGS. 4A, 4B and 4C show stripe patterns S on the display means 5 which are used for optometry, and in this case, the directions and pitches of the stripe patterns S vary. The stripe pattern is gradually enlarged from the initial state of FIG. 4A to the states of FIGS. 4B and 4C and the pitch thereof widens. As in the case of FIGS. 2A to 2C, when the examinee bring down the operating rod 1 and responds in that direction at a point in time at which he or she has visually recognized the direction of the Landolt ring, a response mark B as shown in FIG. 5 which indicates the direction in which the examinee has responded is displayed, and if the direction of response is wrong, the stripe pattern S will be continuedly enlarged, and if the direction of response is right, a stripe pattern in another direction will be presented and a similar process will be repeated.

In this manner, the Landolt ring L or the stripe pattern S is presented as a visual target mark, and on the basis of the size or the pitch when the examinee has correctly responded, calculation is effected by the signal processing means 3 to thereby determine the examinee's eyesight.

The Landolt ring L visual targets of four or eight different directions are used. Measurement is effected by consecutive presentations of a Landolt ring L of at least three different directions. The stripe patterns S used have been described as a plurality of stripe patterns having their directions fixed, but it is also possible to use a movable stripe pattern S. That is, stripe patterns moving in the direction perpendicular to the stripe are used. Eight different responses for the stripe patterns of four different directions will become possible. Such movement of the stripe pattern S leads to the advantage that visual recognition for examinees becomes easy.

As the first visual target mark, the smallest visual target mark of a predetermined direction is presented and gradually enlarged. As the second visual target mark presentation is started not from the smallest visual target mark, but from a visual target mark somewhat smaller than the marksize in first correct response, the time required for measurement can be shortened.

Figure 6A:
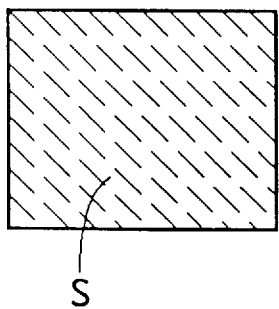
FIGS. 6A, 6B and 6C are illustrations of a stripe pattern visual target with different contrasts.
Figure 6B:
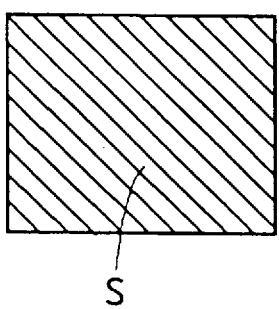
Figure 6C:
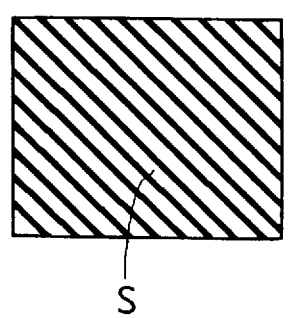

FIGS. 6A, 6B and 6C show a stripe pattern S for the measurement of a contrast threshold value or a spatial frequency characteristic (MTF). Presentation is started with a stripe pattern S of low contrast, and the contrast of the stripe pattern S is gradually increased from FIG. 6A to FIGS. 6B and 6C. At a point in time at which the examinee has visually recognized the stripe pattern S, the examinee inputs that direction and responds, and if the response is wrong, the contrast will be further increased, and if the response is right, the result is registered in the signal processing control means 13 and then a stripe pattern S of another pitch and another direction will be presented. The processes are repeated for various pitches, and the contrast threshold value is calculated from the correct responses for stripe patterns of various pitches.

In this case, it is desirable to vary the direction of the stripe pattern S at random relative to the direction presented last time. By varying the pitch of the stripe pattern S and repeating measurement, it is possible to find the contrast threshold values at respective spatial frequencies. In the foregoing description, the stripe pattern S has been described as being usually fixed, but it is also possible to use a stripe pattern moving in a direction perpendicular to the stripe.

Figure 7:
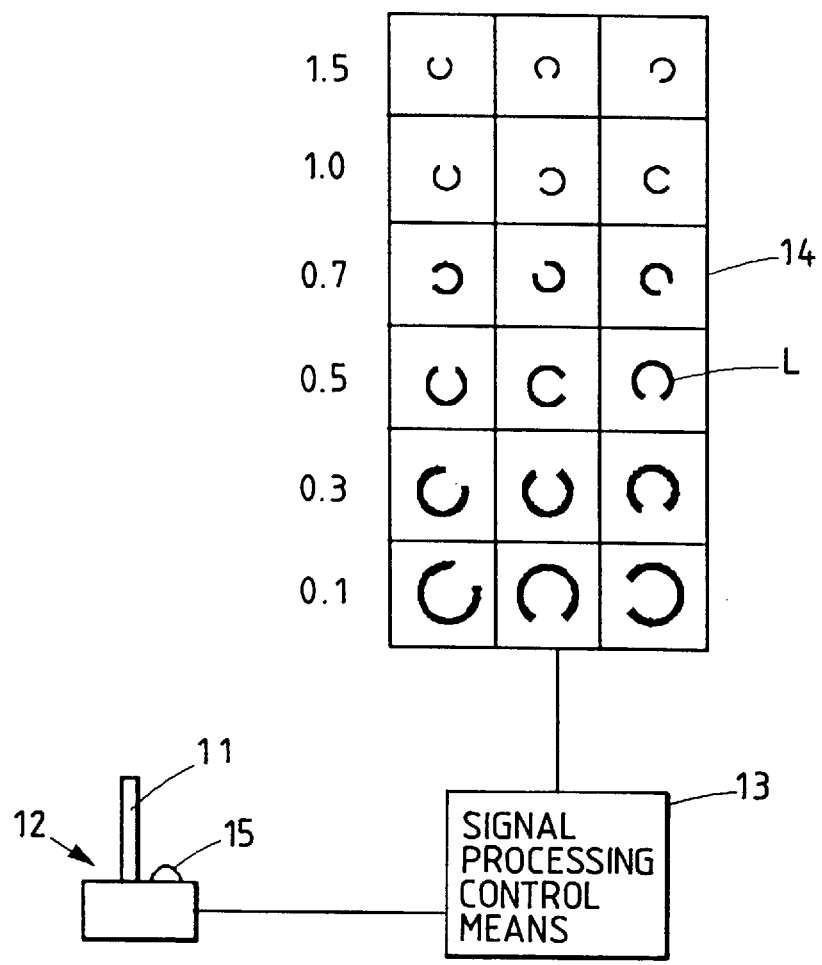
FIG. 7 shows the construction of a second embodiment of the present invention.

Referring now to FIG. 7 which shows the construction of a second embodiment, the output of response means 12 having an operating rod 11 is connected to signal processing control means 13, the output of which in turn is connected to a visual target plate 14 for displaying a plurality of Landolt rings L. The response means 12 is provided with the operating rod 11 for inputting the directions of the Landolt rings L and an invisible button 15 adapted to be depressed for an invisible visual target. The Landolt rings L can be one by one turned on and are required to be responded to.

By the signal processing control means 13, the Landolt ring L of a mark on the visual target plate 14 is turned on in accordance with a predetermined program and is presented to the examinee. The examinee operates the operating rod 11 or the invisible button 15 of the response means 12 to thereby effect a response, and the signal processing control means 13 effects calculation by signals from the response means 12, whereby the examinee's eyesight is determined, and the result is outputted in appropriate recording means, such as a printer.

Numerical values displayed on the left side of the visual target plate 14 are for illustrating eyesight values, and in FIG. 7, they are displayed divisionally at six stages, but actually, they are displayed at ten stages of every 0.1 between 0.1 to 1.0 and two stages 1.2 and 1.5 above them, for a total of twelve stages, and the upper ⅓, middle ⅓ and lower ⅓ of the Landolt ring L are used as visual targets of a small mark, a medium mark and a large mark from above.

As described above, actually the visual target 14 is separated into a total of 36 sections comprising 12 vertical stages and 3 lateral rows, but for the convenience of description, in FIGS. 7, 8A, 8B, 8C and 8D, illustrations are made with a total of 18 sections comprising 6 vertical stages and 3 lateral rows. The visual target plate 14 is sequentially turned on in accordance with a predetermined program, whereby the Landolt rings L within the sections are presented to the examinee. The directions of breaks in the Landolt rings L are irregularly disposed within the respective sections, and further, it is also possible to change the combination of the whole during each measurement.

In measurement, the examinee responds to the direction of the presented Landolt ring L by bringing down the operating rod 11 of the response means 12 in that direction. If the examinee cannot visually recognize the direction of the Landolt ring L and has depressed the invisible button 15 or if there has been no response within a predetermined time or if the response is wrong, the mark x is displayed as a wrong response, and if the response is right, the mark o is displayed as a right response, Arrows in FIGS. 8A to 8D indicate the order of measurement.

In FIG. 8A which shows the measurement procedure according to a first program, the Landolt ring L of eyesight 1.5 in the uppermost stage in the left column is first presented to show that the examinee's response is a wrong response. Next, the Landolt ring L of eyesight 1.0 next to the uppermost stage is presented, and if the response is likewise wrong, larger Landolt rings L in the lower stages, stage-by-stage, are presented. The Landolt ring L proceeds to the stages of eyesight 0.5 and eyesight 0.3, and when the examinee visually recognizes the Landolt ring L of eyesight 0.3 and his or her response becomes a right response, the Landolt ring L moves to the eyesight value in the lateral row upper by one stage, and in this case, the Landolt ring L of eyesight 0.5 in the middle column is presented. This becomes a wrong response and the Landolt ring L of eyesight 0.3 in the stage lower by one stage in the middle column is presented, and this becomes a right response. When two right responses have thus been input for the same eyesight in that stage, the eyesight value in that stage is determined as the examinee's eyesight.

Likewise in FIG. 8B, measurement is started from the eyesight 1.5 of the uppermost stage in the left column. When wrong responses continue as eyesight 1.5, eyesight 1.0 and eyesight 0.7 and a right response comes at the next eyesight 0.5, measurement proceeds to the eyesight 0.7 of the stage above that stage by one stage in the middle column. When a right response also is input here, measurement further proceeds to the eyesight 1.0 of the stage still above that stage by one stage in the right column. When a wrong response is input here, measurement proceeds to the eyesight 0.7 of the stage below that stage by one stage, and when a right response is input here, the examinee's eyesight is determined as 0.7.

FIG. 8C shows the measurement procedure by a second program. When there is a right response, measurement proceeds in a lateral row and if a right response continues twice in the same stage, measurement proceeds to the eyesight value of the stage above that stage by one stage. In the case of a wrong response, measurement proceeds to the eyesight value of the stage below that stage by one stage as in the first program. Measurement is started from the eyesight 1.5 of the uppermost stage in the left column, and proceeds to eyesight 1.0 and eyesight 0.7, and when a right response is input here, measurement proceeds laterally, and when there is a right response at the eyesight 0.7 in the middle column, measurement moves up by one stage, and when a wrong response is input at eyesight 1.0, the examinee's eyesight is determined as 0.7.

FIG. 8D shows the measurement procedure by a third program. Measurement is started from eyesight 1.0 in the left column, and this program is the same as the second program in the other points. If eyesight 1.0 is a right response, measurement proceeds laterally, and when a right response comes for eyesight 1.0 in the middle column, measurement proceeds upwardly and when a right response comes for eyesight 1.5, measurement proceeds laterally, and when there is a right response for eyesight 1.5 in the right column, the examinee's eyesight is determined as 1.5.

FIGS. 9A, 9B and 9C show the display screen of the visual target 14 in a third embodiment. As the visual target 14, use is made of a television monitor or a liquid crystal plate for image display or the like, and design is made such that visual target mark patterns M comprising character E are generated on the screen by the use of a pattern generating circuit. In the other points, the construction of the third embodiment is the same as that of the second embodiment.

To the examinee, presentation is started from the smallest visual target mark M, and as shown in FIG. 9A, a plurality of visual target marks M are displayed on the screen. The examinee's adjustment will not be sufficiently stable if the design is made such that only a single small visual target mark M is displayed, and therefore the design is thus made such that a plurality of visual target marks M of the same size are displayed.

If there is no response for a predetermined time, the pattern on the screen is gradually enlarged, and as shown in FIG. 9B, a central visual target mark M and partly broken visual target marks M around it are displayed, and then the screen is further enlarged and as shown in FIG. 9C, only a large visual target mark M is displayed at the center.

When the examinee cannot visually recognize the visual target mark M, he or she does not respond or responds by means of the invisible button 15, and when he or she has visually recognized the visual target mark M, he or she responds in that direction by means of the response means 12. When there is an invisible response or when there is a wrong response by direction inputting, the same visual target mark M is further enlarged and the enlargement is continued until a response input in a correct direction is obtained. When a right response is obtained, the size of the visual targe mark M is registered in the apparatus. The mark is then changed to a small visual target mark M in another direction, and this visual target mark M is enlarged until there is again a right response. This is repeated two to three times for visual target marks M of different directions, and the examinee's eyesight is determined in the signal processing means from the sizes of visual target mark M for which there have been right responses.

As described above, the invisible button 15 is provided so that the examinee may make an invisible response when he or she can not visually recognize the visual target mark and therefore, the frequency of responding in the direction of the visual target mark M by the response means 12 decreases and it becomes possible to generally shorten the measuring time.

Also, if the design of the device is made such that the presentation of the second and subsequent visual target marks M is started from a visual target mark M of a size smaller by the order of two stages than the target size of the previous right response measurement, the measuring time could be shortened. Also, if the design of the device is made such that a response mark as in FIG. 3 is displayed on or near the visual target screen 14, the examinee could confirm that he or she is responding in a direction intended by him or her.

The visual target patterns M are displayed for 1 to 3 seconds when there is no response and if an electronic sound or the like is generated when visual target patterns are changed, it allows the examinee to concentrate on the examination.

In the visual function measuring apparatus according to each of the above-described embodiments, a visual target is presented onto the visual target display means by the visual target generating means and the size or contrast thereof is varied and on the basis of the examinee's response signal, the visual function is found by the signal processing control means, whereby the examinee himself can measure his or her visual function such as eyesight or a contrast threshold value automatically and within a short time.

Also, in the visual function measuring apparatus according to each of the above-described embodiments, the presentation of visual target marks is changed in succession from a smaller one to a larger one, whereby the number of responses for visual target marks can be decreased to thereby generally shorten the measuring time. Efficient and accurate measurement of eyesight, therefore, becomes possible.

Figure 10:
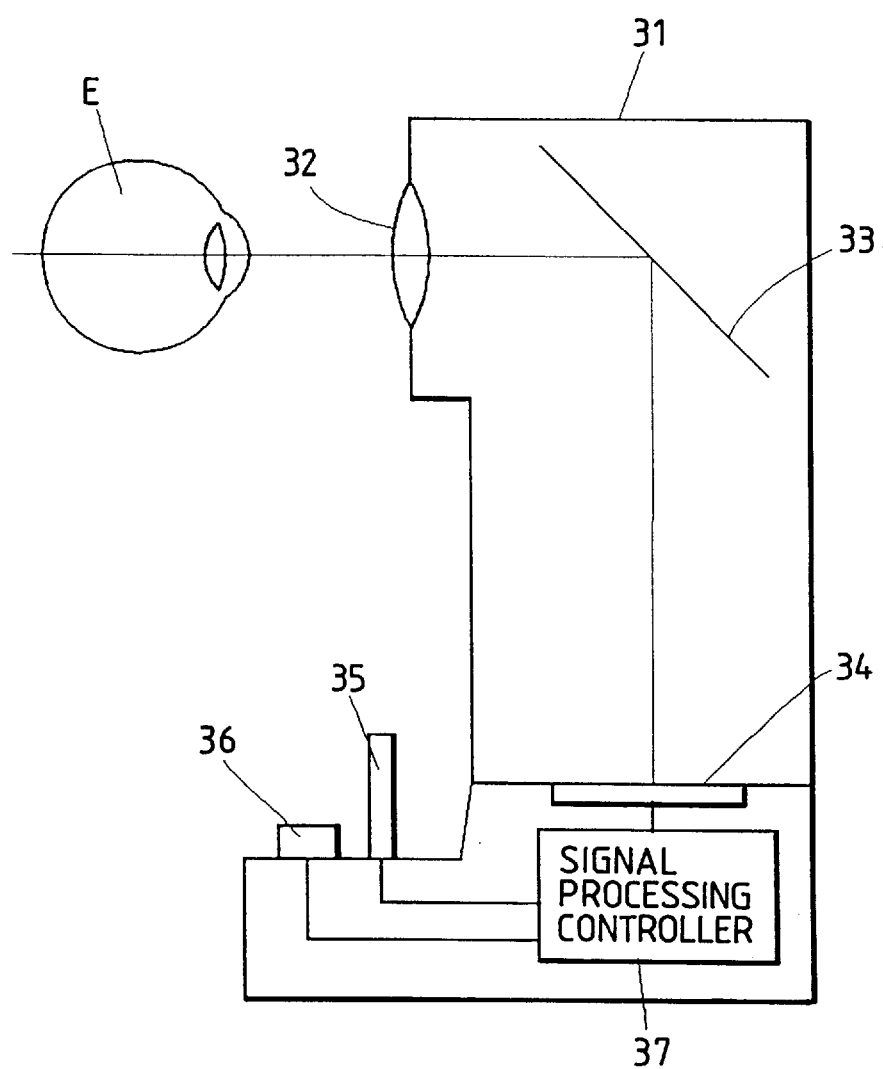
FIG. 10 shows the construction of a fourth embodiment of the present invention.

Referring now to FIG. 10, which shows an automatic eyesight meter according to a fourth embodiment, an objective lens 32 is provided at a location in the upper portion of the automatic eyesight meter 31 which is opposed to an eye E to be examined, a mirror 33 is disposed behind the objective lens 32, and a liquid crystal image display 34 is disposed in the incidence direction of the mirror 33. An operating rod 35 which is a direction response means and a stop button 36 which is a stop response means are provided at the examinee's hand in the lower portion of the automatic optometer 31, and the outputs of the operating rod 35 and stop button 36 are connected to a signal processing controller 37, the output of which in turn is connected to the liquid crystal display 34.

Figure 11:
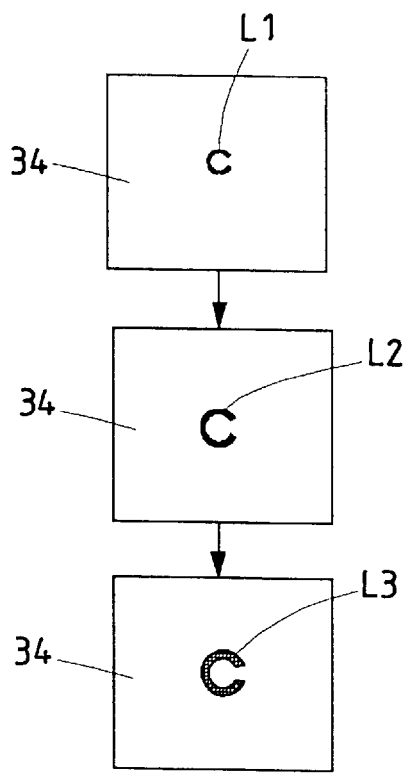
FIG. 11 illustrates changes in a visual target.

The signal processing controller 37 generates a visual target comprising a Landolt ring as shown in FIG. 11 on the liquid crystal display 34 and presents it to the eye E to be examined through the intermediary of the mirror 33 and objective lens 32. At the early stage of the measuring process, presentation is started from the smallest visual target to determine the rough level of the eyesight value. That is, the visual target in a predetermined direction is presented while its size is changed in succession from a small visual target L1 to larger visual targets L2 and L3 as shown in FIG. 11.

When the visual target assumes a visible size, the examinee depresses the stop button 36, whereby the change in the size of the visual target is stopped. Subsequently, the examinee responds in the direction of this visual target by bringing down the operating rod 35 in the direction of the break in the Landolt ring. If this is a right response, the visual target again changes gradually from the smaller one to the larger one in a direction differing from the first-mentioned direction and therefore, when the visual target has again become visible, the examinee depresses the stop button 36 and inputs the direction by means of the operating rod 35.

In the second presentation, the presentation is started from a visual target somewhat smaller than the one to which the examinee responded rightly the first time, and a measuring process similar to the first time is repeated. The process is repeated three to five times with the visual targets of different directions, and on the basis of the size of a visual target to which the examinee has responded rightly, the eyesight value is determined by the signal processing controller 37. When the examinee has responded in a wrong direction, the visual target again changes so as to become larger after the response, and when the examinee has seen the visual target, he or she depresses the stop button 36 again and inputs the direction by means of the operating rod 35.

If the examinee can make a response rapidly, he or she may respond only by the operating rod 35 without using the stop button 36, and in such case, the change in the size of the visual target may be stopped for about a second if the operating rod 35 is moved by any amount, and direction may be inputted during the time. Also, the design of the device is such that when the apparatus has recognized and registered the response input, it is indicated by sound or the like and therefore, during the time till then, the input direction of the operating rod 35 can be changed. Further, the design of the device is such that if there is no direction response within a predetermined time of e.g., five seconds after the stop button 36 has been depressed, the change for the enlargement of the visual target is resumed. Like this, the operating rod 35 can be used also for stop response. Also, various visual targets are stored in the memory of the signal processing controller 37 and therefore, measurement progresses in such a manner that they are successively presented in accordance with a program.

Figure 12:
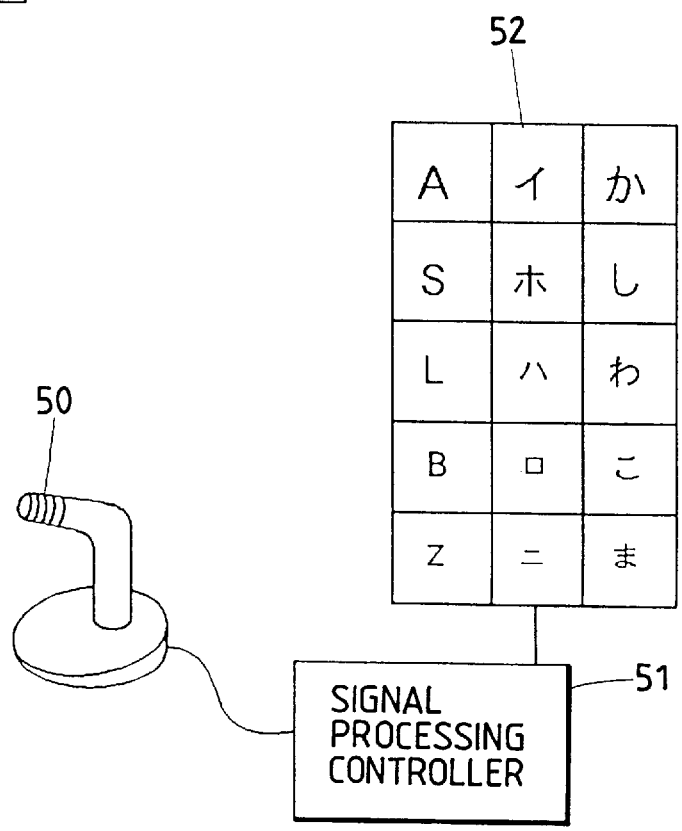
FIG. 12 shows the construction of a fifth embodiment of the present invention.

FIG. 12 shows an automatic eyesight meter according to a fifth embodiment. A microphone 50 as response means is provided at the examinee's hand, and the output of the microphone 50 is connected to a signal processing controller 51 having a voice recognizing portion, the output of the signal processing controller 51 being connected to a visual target displaying portion 52.

The visual target displaying portion is provided with visual targets of e.g. five stages differing in size and arranged from above in the order of sizes, and three kinds of visual targets are provided for each stage. Each visual target is designed to be capable of being illuminated from behind it by a lamp, not shown, and it may be known to the examinee that the visual target illuminated by the lamp is a presented visual target.

The examinee reads the visual target illuminated by the lamp, and when he or she Inputs a response by voice, the voice is inputted to the signal processing controller 51 through the microphone 50 and is deciphered by the voice recognizing portion in the signal processing controller 51, and whether the response is right is judged. When measurement is started, lamps are turned on in succession from the lowermost stage, and when the examinee has seen a visual target, he or she responds in such a manner as to utter any voice. If at this stage, there is a voice input of a predetermined level or higher, the signal processing controller 51 understands that the examiner has "seen" the visual target. Thereafter, the visual targets near the seen one are presented one by one and the examinee continues to respond to them by voice, and the examinee's eyesight is determined by whether they are right or wrong.

As described above, in the embodiments, up to the vicinity of the eyesight value or the refractive value of the eye E to be examined is specified at the first stage of screening, whereafter examination is made by a visual target of a size or visibility approximate thereto, whereby the frequency of response can be decreased to thereby shorten the measuring time. Further, the operating time is shortened more by the stop response of depressing the stop button than by the operation in the prior art wherein only the direction response is made by bringing down the operating rod, and even if an operation is effected with the speed of change in the visual targets increased, a judgment is formed with the visual targets stopped, whereby a reliable response can be executed within a short time.

According to the embodiments described above, the automatic visual function measuring apparatus presents visual targets to the examinee while changing them in succession from a smaller visual target or stripes of weaker contrast to a larger visual target or stripes of stronger contrast, and the examinee makes a response when he or she has seen a visual target or stripes and therefore, the entire measuring time can be shortened and efficient eyesight measurement can be accomplished.

What is claimed is:

1. A visual function measuring apparatus comprising:
    visual target displaying means for presenting visual targets of different sizes successively to an eye to be examined;
    response inputting means for inputting the response of an examinee to whom the visual targets have been presented, the examinee's visual function being measured on the basis of the response input; and
    control means for controlling said visual target displaying means to change, in succession, the visual targets presented to the examinee from a smaller visual target to a larger visual target,
    wherein the examinee's visual function is measured on the basis of the response input by the examinee during the changing of the visual targets from the smaller visual target to the larger visual target in succession, and wherein said control means controls said visual target displaying means to change the manner in which the visual targets are presented when the response input by the examinee occurs.

2. The apparatus according to claim 1, wherein said control means makes the visual targets presented by said visual target displaying means larger by one stage when the response input to said response inputting means is a non-response of a predetermined time, or a wrong response or an indistinct response.

3. The apparatus according to claim 1, wherein said control means makes the visual targets presented by said visual target displaying means smaller when the response input to said response inputting means is a right response.

4. The apparatus according to claim 1, wherein said presented visual targets are marks having directionality, or stripe patterns, and said response inputting means has direction inputting means for inputting the directions of the presented visual targets.

5. The apparatus according to claim 4, wherein said response inputting means further has indistinct response means for responding to non-visual recognition.

6. The apparatus according to claim 1, wherein said control means stops the change of the presented visual targets temporarily in response to the input of said response inputting means.

7. The apparatus according to claim 1, wherein said response inputting means has voice inputting means.

8. The apparatus according to claim 1, wherein said visual target displaying means displays a plurality of visual targets of the same shape at time.

9. The apparatus according to claim 1, wherein said visual target displaying means has a liquid crystal display.

10. A visual function measuring apparatus comprising:
    visual target displaying means for presenting a visual target to an eye to be examined;
    response inputting means for inputting the response of an examinee to whom the visual target has been presented; and
    control means for controlling said visual target displaying means to sequentially vary the size of the visual target presented to the examinee, wherein the examinee's visual function is measured on the basis of the size of the visual target when correct responses are input to said response inputting means by the examinee during the sequential changing of the size of the visual target, and wherein said control means controls said visual target displaying means to chance the manner in which the visual target is presented when the response input by the examinee occurs.

11. The apparatus according to claim 10, wherein said visual target is a mark having directionality, and said control means varies the size of said mark.

12. The apparatus according to claim 10, wherein said visual target is a stripe pattern, and said control means varies the pitch of said stripe pattern.

13. A visual function measuring apparatus comprising:

visual target displaying means for presenting a visual target to an eye to be examined;

response inputting means for inputting the response of an examinee to whom the visual target has been presented;

control means for controlling said visual target displaying means to sequentially change the size of the visual target presented to the examinee by said visual target displaying means; and stop means for once stopping the sequential change of the size of the presented visual target by a predetermined input by the examinee,
wherein the examinee's visual function is measured on the basis of the presented visual target when a response is input to said response inputting means by the examinee.

14. The apparatus according to claim 13, wherein said control means varies the presentation visibility of the presented visual target.

15. The apparatus according to claim 13, wherein said stop means stops the change of the visual target on the basis of said response inputting means.

* * * * *

UNITED STATES PATENT AND TRADEMARK OFFICE
CERTIFICATE OF CORRECTION

PATENT NO. : 5,825,460
DATED : October 20, 1998
INVENTOR(S): YOSHIMI KOHYAYAKAWA It is certified that error appears in the above-identified patent and that said Letters Patent is hereby corrected as shown below:

COLUMN 2:

Line 42, "bring" should read --brings--.

COLUMN 3:

Line 6, "first" should read --the first--.

COLUMN 5:

Line 37, "targe" should read --target--.

COLUMN 6:

Line 55, "to" should read --to that carried out--.

COLUMN 7:

Line 36, "Inputs" should read --inputs--.
Line 43, "any" should read --an input by--.
Line 46, "examiner" should read --examinee--.
Line 50, "they" should read --the responses--.

UNITED STATES PATENT AND TRADEMARK OFFICE
CERTIFICATE OF CORRECTION

PATENT NO. : 5,825,460

DATED : October 20, 1998

INVENTOR(S) : YOSHIMI KOHAYAKAWA

It is certified that error appears in the above-identified patent and that said Letters Patent is hereby corrected as shown below:

COLUMN 8:

Line 55, "at" should read --at a--.

COLUMN 9:

Line 6, "chance" should read --change--.

Signed and Sealed this

Seventeenth Day of August, 1999

Q. TODD DICKINSON

*Attest:*

*Attesting Officer*      *Acting Commissioner of Patents and Trademarks*